United States Patent
Maaskamp

(10) Patent No.: US 6,585,708 B1
(45) Date of Patent: Jul. 1, 2003

(54) FLOW CONTROL SYSTEM AND METHOD FOR ENDOSCOPIC SURGERIES

(76) Inventor: Armand Maaskamp, 22315 Clearbrook, Mission Viejo, CA (US) 92692

(*) Notice: Subject to any disclaimer, the term of this patent is extended or adjusted under 35 U.S.C. 154(b) by 208 days.

(21) Appl. No.: 09/709,430

(22) Filed: Nov. 13, 2000

Related U.S. Application Data

(62) Division of application No. 09/099,813, filed on Jun. 19, 1998, now Pat. No. 6,149,633.
(60) Provisional application No. 60/052,593, filed on Jul. 15, 1997.

(51) Int. Cl.[7] .............................................. A61M 1/00
(52) U.S. Cl. ........................ 604/317; 604/35; 600/573; 137/605
(58) Field of Search ................................ 604/317–320, 604/118–119, 327, 246; 128/898; 137/605

(56) References Cited

U.S. PATENT DOCUMENTS

| | | |
|---|---|---|
| 3,885,565 A | 5/1975 | Stachell |
| 4,504,266 A | 3/1985 | Harle |
| 5,395,354 A | 3/1995 | Vancaillie |
| 5,492,537 A | 2/1996 | Vancaillie |
| 5,599,333 A | 2/1997 | Atkinson |
| 5,720,299 A | 2/1998 | Theodoru |
| 5,827,229 A | 10/1998 | Auth et al. |
| 5,890,516 A | 4/1999 | Talamonti |

*Primary Examiner*—Dennis Ruhl
*Assistant Examiner*—Linh Truong

(57) ABSTRACT

In a system which utilizes an endoscope and irrigation fluid during surgery within a body orifice, and in which irrigation fluid is withdrawn via a principal path into a suction canister, there is a substantially constant suction and withdrawal rate from the operative site to limit absorption of irrigation fluid within the patient, because a bifurcated flow path that leads to the suction canister not only from the endoscope but also from a drain bag receiving overflow from the body orifice via a tailored drape includes a substantially greater flow impedance in the drain bag path. The common suction line joined to the endoscope line and the drain bag line draws a flow through the endoscope that predominates, to maintain substantially constant withdrawal of irrigation fluid via that path, and substantially eliminates the possibility of loss of suction.

9 Claims, 3 Drawing Sheets

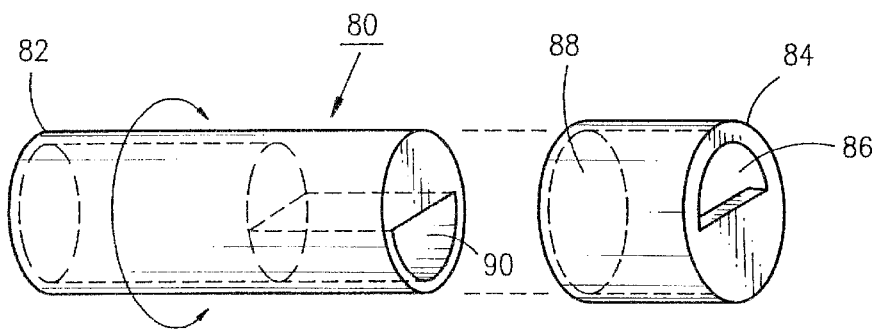
FIG. 5a
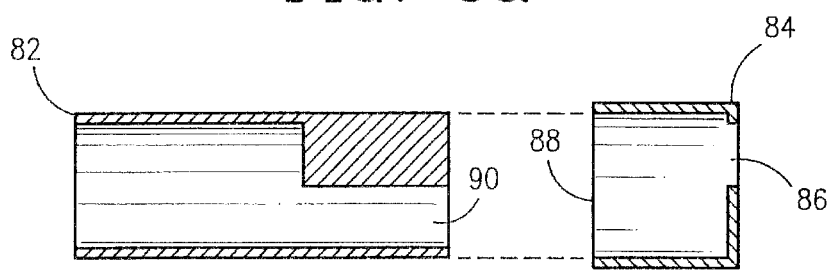
FIG. 5b
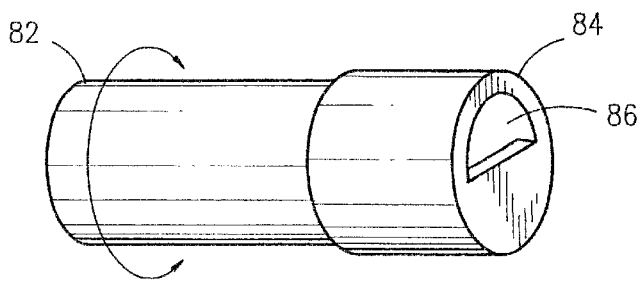
FIG. 5c
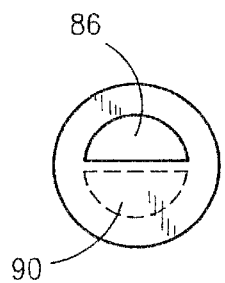 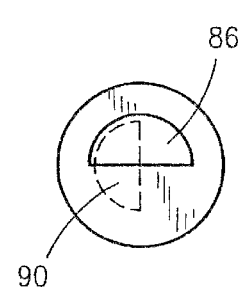 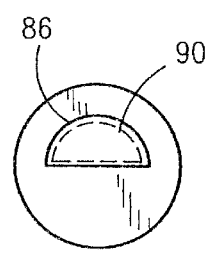
FIG. 5d    FIG. 5e    FIG. 5f

FLOW CONTROL SYSTEM AND METHOD FOR ENDOSCOPIC SURGERIES

CROSS-REFERENCE TO RELATED APPLICATIONS

Embodiments of this invention relate to Provisional Application Serial No. 60/052,593, filed Jul. 15, 1997. The contents of that application are incorporated by reference herein. This application is a division of application Ser. No. 09/099,813 filed Jun. 19, 1998 now U.S. Pat. No. 6,149,633.

BACKGROUND OF THE INVENTION

1. Field of the Invention

This invention relates to apparatus and methods used in specialized, minimally invasive surgery, and more particularly to techniques for minimizing the amount of fluid absorbed within a patient during surgeries utilizing irrigation flows.

2. Description of Related Art

Laparoscopic techniques for performing certain surgical procedures have been widely adopted because they often simplify a given operation, reduce the trauma to the patient, and shorten recovery time. In procedures such as hysteroscopy and prostatectomies using trans-urethral resection, the operative site must be constantly irrigated as the surgeon views the site through an endoscope while manipulating the laparoscopic instruments. Irrigation is essential not only to visualization, but also to transporting surgical debris, blood and tissue, away from the site. However, as pointed out in U.S. Pat. No. 5,492,537 to Vancaillie ("the '537 patent"), there are problems associated with such procedures. Because some of the fluid will be absorbed in the body instead of being transported away, there is a danger of pulmonary edema or electrolytic imbalance if too much fluid is absorbed. Consequently, the '537 patent discloses a fluid monitoring system which determines, on an ongoing basis, the amount of fluid absorbed by measuring the mass of fluid supplied from a source and the mass of fluid collected from the operative site. If indications are that too much fluid is being absorbed, measures can be taken.

The system of the '537 patent operates by using gravity to feed irrigation fluid from an elevated source to a fluid source channel in the probe used by the surgeon to observe the operative site. Concurrently, irrigation fluid is collected from the operative site via a fluid collection channel in the probe, while overflow from the operative site proceeds outwardly through the body orifice into a fitted drape system feeding a funnel-like drain bag. The fluid from the collection channel and drain bag is drawn into collection canisters by a common negative pressure source for disposal or examination. By monitoring the weight of the source fluid delivered and waste fluid collected, the system can calculate an approximate value for fluid absorbed.

A high irrigation flow rate is needed to insure full lavage and adequate visibility at the operative site. To minimize absorption of fluid within the patient and the passage of fluid from intravascular to interstitial spaces, outflow of fluid through the probe's collection channel (and therefore the negative pressure or suction level in the channel) must be substantial and continuous. In practice, however, this result is not readily achieved. Where the suction force in the probe collection channel and the drain bag are produced by the same negative pressure source, as in the '537 patent, suction forces generated by the negative pressure source are often powerful enough to keep the drain bag empty. As a result, the open drain line and empty drain bag can draw large quantities of air, taxing the suction capabilities of the negative pressure source and reducing the suction force in the probe collection channel and at the probe tip. Consequently, suction at the operative site can be partially lost, resulting in both excessive fluid absorption in the body and diversion of excess fluid into the drain bag.

SUMMARY OF THE DISCLOSURE

Systems and methods in accordance with the invention employ a bifurcated tubing system joined at a junction that leads to a single line feeding into a suction canister system that creates an imbalance within a predetermined range between the suction drawn at the scope collection channel and the suction available at the drain bag. To create this imbalance, the flow path in the branch of the bifurcated system between the junction and the drain bag is of substantially higher flow impedance than the conduit to the scope collection channel. Suction forces acting on the irrigation fluid withdrawn from the operative site are thus substantially higher in the scope collection channel, and therefore the scope collection channel transports the majority of fluid away from the operative site. This in turn assures superior clarity and easier visualization within the operative site, and reduces the amount of overflow from the body orifice (vagina or urethra). Consequently, gravity flow into the drain bag is reduced, and even though the flow is restricted, the suction acting at the bottom of the drain bag is adequate to empty fluid collected in the drain bag. The higher flow impedance can be established at a selected level by a reduced diameter section, a tubing of smaller inner diameter or a resiliently deformable member responsive to pressure, each being configured to provide the proper balance of flows given overall flow impedances, but designed to be compatible with a low cost disposable system.

Methods in accordance with the invention combine separate outflows of irrigation fluid from a body cavity, the flow paths each being arranged to exert suction from a common source in a different manner. The suction in a principal flow path through a probe in the cavity and a port in an endoscope or other device is kept substantially constant at a level which withdraws the majority of the irrigation fluid, thus minimizing absorption of fluid within the patient and enabling improved observation through the endoscope. It also reduces overflow from the body cavity, some of which is inevitable, into a fitted drape on the patient, and then into a drain bag, under gravity forces. Suction on the bottom of the drain bag is exerted from the common source, but the flow rate is limited, which insures that suction on the principal line is not reduced.

BRIEF DESCRIPTION OF THE DRAWINGS

A better understanding of the invention may be had by reference to the following description, taken in conjunction with the accompanying drawings, in which:

FIG. 5a is a exploded perspective view of a variable flow restrictor that may be used in the system of FIGS. 1 and 2.

FIG. 5b is a side view, partially broken away, of a variable flow restrictor that may be used in the system of FIGS. 1 and 2.

FIG. 5c is a perspective view of a variable flow restrictor that may be used in the system of FIGS. 1 and 2.

FIGS. 5d–f are symbolic representations of the alignment of openings in a variable flow restrictor that may be used in the system of FIGS. 1 and 2.

DETAILED DESCRIPTION OF THE PREFERRED EMBODIMENTS

Figure 1:
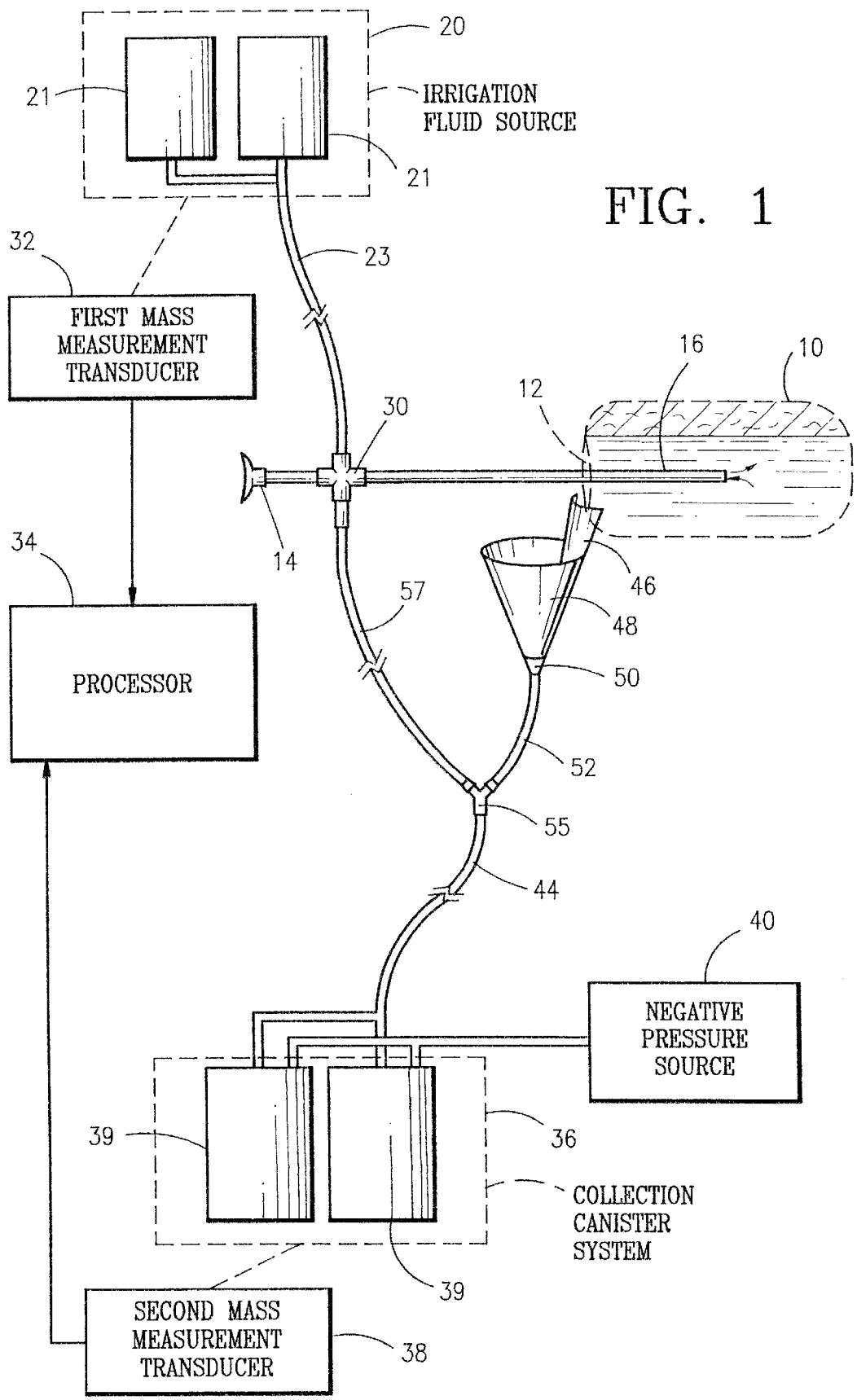
FIG. 1 is a generalized and simplified representation of an irrigation fluid transport system in accordance with the invention for use in an endoscopic surgical procedure.
Figure 2:
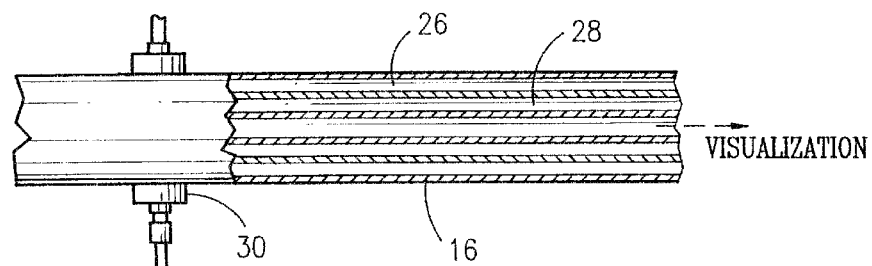
FIG. 2 is an enlarged view of a portion of a bifurcated fluid withdrawal arrangement used in the system of FIG. 1.

In the example of FIGS. 1 and 2, which illustrates in somewhat simplified and idealized form the principal elements and arrangements used in a typical endoscopic surgery, the specialized laparoscopic instruments normally employed have been omitted for clarity and simplicity. These instruments are inserted into a target body cavity 10 through a body orifice 12, shown symbolically. The operation described by way of example is assumed to comprise a hysteroscopy, in which event the body orifice 12 is the vagina, or a trans-urethral resection of the prostate (prostatectomy), in which event the body orifice 12 is the urethra. The surgeon views the interior of the operative site 10 via an endoscope 14 attached to an extended probe 16 which is placed within the interior cavity. A source of irrigation fluid 20, which may comprise one or more bottles or bags 21, is elevated above the operative site at a distance chosen to provide a given irrigation flow pressure. In one embodiment of the invention, the elevation is about 100 cm above the operative site and the flow is in the range of 60–150 ml/min. The line or lines 23 from the source are connected into an intermediate region of the probe 16, so that the irrigation fluid flows through a longitudinal irrigation channel 26 (FIG. 2) into the intra-cavity operative site. From within the cavity, fluid is withdrawn through an aspiration channel 28 (FIG. 2) in the probe 16 back to a midregion outlet port 30. The specific endoscopic instrument and probe that can be used are a matter of choice, as long as irrigation and aspiration flow paths are provided, along with means for visualizing the cavity 10 interior during the procedure.

Overflow from the body orifice 12 is collected by a tailored drape unit 46 about and below the body orifice 12, and secured as by surgical tape (not shown) to the body curvatures so as to minimize spillage and lost fluid. The drape 46 leads to a funnel-shaped drain bag 48 that directs fluid by gravity flow downwardly to a bottom connector 50 leading to a drain line 52 in a bifurcated conduit system. The drain line 52 leads from the bottom connector 50 of the drain bag 48 to a "Y" junction 55, and a second, longer line or tubing 57 leads from the outlet port 30 on the endoscope 14 to the other input port of the "Y" junction 55. The outlet at the base of the common suction line 44 is coupled to the parallel inputs of the suction canisters 39, the interior of each capable of being held under negative pressure in a fashion common to a number of different irrigation/aspiration systems. As one canister is filled, flow automatically continues to the next in the series until the operation is completed.

Fluid absorption is monitored in part by a transducer 32, which supplies signals to a processor 34 based on the weight of irrigation fluid in the irrigation fluid source 20. By measuring both the initial weight of the irrigation fluid source 20 and the weight of the irrigation fluid source 20 after a period of time, the weight of the fluid delivered can be computed. The weight of aspirated fluid received in the collection canister system 36 after the same period of time is also measured by transducer 38, and responsive signals are provided to the processor 34. By subtracting the weight of aspirated fluid from the weight of the fluid delivered, the weight of fluid absorbed can be computed.

Figure 3:
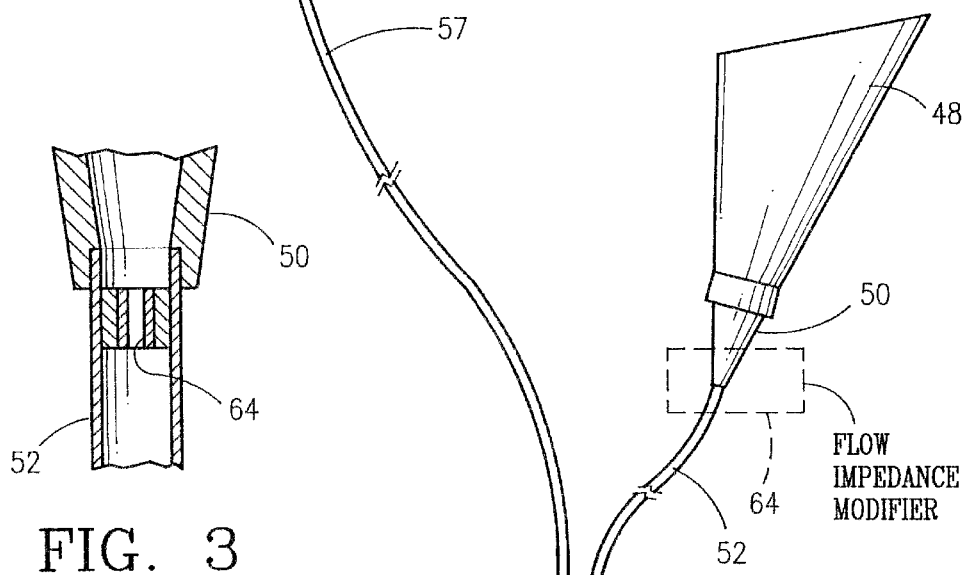
FIG. 3 is a fragmentary perspective view, partially broken away, showing details of a flow impedance control that may be employed in the example of FIGS. 1 and 2.

Operations of these kinds can continue for hours, often with an absorption rate as high as 10–30 ml/min. Over the span of a two-hour operation, patients may absorb as much as 6–8 liters of fluid. Consequently, a number of different irrigation fluid bags 21 are used to provide adequate capacity (about 30 liters) for the duration of the procedure, allowing for the possibility of adding more irrigation fluid. In these systems, the gravity head supplying irrigation fluid to the operative site is of the order of 100 cm of $H_2O$, and the suction level at the canisters is of the order of 10 psi or 700 cm of $H_2O$. The principal tubing branch 57 leading from the endoscope 14 to the suction canisters 36 is of approximately 0.225 inches interior diameter (I.D.), and is about 60" in length. It is coupled to the "Y" junction 55, which is of standard size and low cost. At the opposite end, principal tubing branch 57 is coupled to the outlet port 30 by a rotating male luer connector 60 (FIG. 2). The line 52 from the drain bag 48 is also coupled to standard disposal connectors 50, 55 and is of 0.225" I.D., but is only 12" long. The lengths and I.D.s determine the nominal flow impedances, which would be less for the drain bag line 52 due to its shorter length. Drain line 52, because of its lower flow impedance, will therefore tend to draw more suction than principal tubing branch 57. However, the flow impedance of the drain line 52 branch may be significantly increased by including a small diameter restrictor 64 (FIG. 3) having an opening of 0.062" interior diameter at the outlet side of the connector 50. This may alternatively be introduced at the connector side of the drain bag 48 or within the line 52. Alternatively, the diameter of the opening of the restrictor 64 may be narrower or wider, depending on the flow impedance characteristics of the lines 52 and 57 in the bifurcated system. A lockable finger clamp (not shown) may be disposed on line 52 to achieve the same effect as the restrictor 64, or may be placed on line 57 to terminate aspiration flow through the probe 16 at the surgeon's discretion. The common tubing suction line 44 is relatively long, here about 108 inches, to allow full freedom of placement of the system relative to the patient.

With gravity flow into the drain bag 48, and constant circulation of fluid for lavage within the surgical site, suction must be continually maintained in both paths. The flow control element 64 in the line 52 adjacent the drain bag 48 creates a substantial flow disproportion between the two branches. With the drain line 52 of high flow impedance as compared to tubing line 57, the rate of fluid flow from the operative site through the probe 16, the endoscope 14 and tubing line 57 to the junction 55 and then through the long common suction line 44 is much greater than through drain bag 48, connector 50, flow restrictor 64, and drain line 52. However, because the negative pressure source 40 is substantial, the suction in drain line 52 remains sufficient to substantially immediately withdraw overflow from the drain bag 48 into the canisters 39, even though the flow path is small in cross-section and of high flow impedance. The net result of this flow impedance imbalance is that while sufficient suction remains in drain line 52 to keep the drain bag 48 clear, high and consistent suction forces in the tubing line 57 and at the tip of probe 16 permit much of the irrigation fluid to be removed at the operative site, reducing undesirable fluid absorption by the body.

Figure 4:
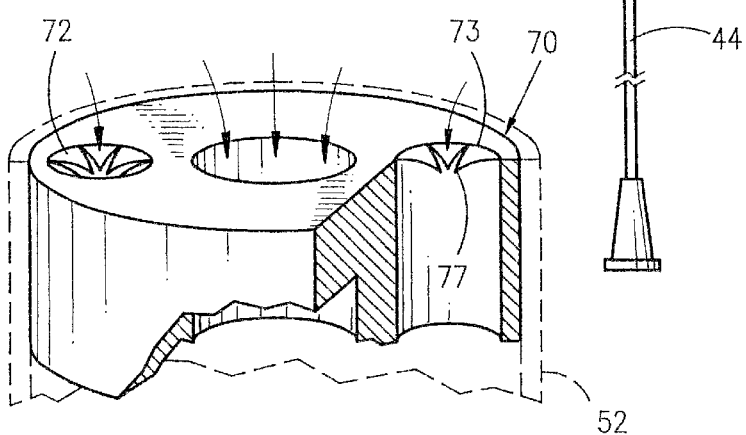
FIG. 4 is a perspective view, partially broken away, of a different form of flow impedance control that may be used in the system of FIGS. 1 and 2.

In the example of FIG. 4, a flow restrictor 70 in the drain bag suction line 52 is supplemented by two resiliently deformable elements 72, 73 covering pressure release tubes 79, each element configured to open somewhat in response to the amount of fluid collected in the drain bag. A constant minimum opening is provided by a small control tube 75, while deformable elements 72, 73 formed of contiguous resilient flaps 77 lie in a substantially transverse plane to the pressure release tubes 79 when under no pressure from fluid weight, effectively blocking the opening to pressure release tubes 79. If the fluid level in the drain bag builds up so as to provide a problem with evacuation or perhaps overflow, deformable flaps 77 yield and lower the flow impedance by opening pressure release tubes 79, enabling increased fluid evacuation until the level drops. Because the deformations are only momentary and increase the flow rate only for a limited time, this arrangement does not affect the high and substantially constant suction and withdrawal rate in the main tubing line 57.

In the example of FIG. 5a–5f, a variable flow restrictor 80 is insertable into drain line 52 (not shown in FIG. 5a–5f). As seen in FIG. 5a, the variable flow restrictor 80 comprises an inner cylinder 82, slidably insertable into outer cylinder 84. In preferred embodiments, the inner cylinder 82 and outer cylinder 84 are formed from a pliable material such as rubber or plastic such that when the inner cylinder 82 is inserted into outer cylinder 84, they are frictionally coupled. The outer cylinder 84 has an duct 86 and a mouth 88 for receiving the inner cylinder 82. The inner cylinder 82 has a port 90 that extends only part of the axial length of the inner cylinder 82, the remainder of the inner cylinder 82 being hollow. By rotating the inner cylinder 82 with respect to the outer cylinder 84, the duct 86 and port 90 will line up to varying degrees, allowing fluid flow through the variable flow restrictor 80.

FIG. 5d shows the duct 86 and port 90 in the complete misalignment of FIG. 5a, allowing no fluid flow. FIG. 5e shows the duct 86 and port 90 in partial alignment, allowing partial fluid flow. FIG. 5f shows the duct 86 and port 90 in complete alignment, allowing the full fluid flow allowable by the variable flow restrictor 80. FIG. 5b is a side view, partially cut away, of the inner cylinder 82 and outer cylinder 84. FIG. 5c is a perspective view of the inner cylinder 82 inserted into outer cylinder 84. Because the inner cylinder 82 does not touch the sides of the drain line 52, the inner cylinder may be squeezed through the drain line 52 and rotated while inserted within the drain line 52, providing a surgeon with the ability to adjust the flow impedance of the drain line 52 to maintain proper suction at the probe tip.

What is claimed:

1. In a fluid flow system for surgery comprising a probe having an aspirating tip coupled by probe tubing to at least one collection canister, a drain receptacle coupled by drain tubing to the at least one collection canister, and a negative pressure source coupled to the at least one collection canister, a method for controlling fluid flow from a surgical site comprising the steps of:

aspirating fluid and organic debris from the surgical site through the probe and probe tubing into the at least one collection canister;

collecting overflow fluid from a body orifice in communication with the surgical site into the drain receptacle through the drain tubing and into the at least one collection canister;

holding the at least one collection canister under negative pressure and producing a suction force through the probe tubing and drain tubing by operation of the negative pressure source; and establishing the flow impedance of the drain tubing as compared to the flow impedance of the probe tubing at a level where the suction force at the probe tip is larger than the suction force at the drain receptacle, such that a majority of irrigation fluid at the surgical site is removed through the probe tip.

2. The method of claim 1, wherein the step of establishing the flow impedance of the drain tubing comprises the step of restricting an inner diameter of a length of the drain tubing.

3. The method of claim 2, wherein the step of restricting an inner diameter of a length of the drain tubing further comprises the step of opening the restricted inner diameter partially in response to fluid weight in the drain tubing.

4. The method of claim 2, wherein the system includes at least one flow opening in the drain tubing and wherein the step of restricting an inner diameter of a length of the drain tubing comprises the step of adjusting the cross-sectional area of the at least one flow opening.

5. The method of claim 2, wherein the step of restricting an inner diameter of a length of the drain tubing comprises the step of externally compressing the drain tubing.

6. In a fluid flow system for endoscopic surgery comprising a probe having an aspirating tip for engagement at a surgical site coupled by probe tubing to at least one collection canister, and a negative pressure source coupled to the at least one collection canister, a method for controlling the relation between the fluid flows from the surgical site during an endoscopic surgery to assure that suction at the probe tip is not lost, comprising the steps of:

aspirating fluid and organic debris form the surgical site through the probe and probe tubing into the at least one collection canister;

collecting overflow fluid from a body orifice in gravity communication with the drain receptacle and flowing through the drain tubing and into the at least one collection canister;

holding the at least one collection canister under negative pressure and producing a suction force through the probe tubing and drain tubing by operation of the negative pressure source; and increasing the flow impedance of the drain tubing as compared to the flow impedance of the probe tubing to a level where the suction force acting on the fluid in the drain tubing provides restricted flow such that the fluid in the drain tubing is not completely withdrawn and that suction remains at the probe tip.

7. In a fluid flow system endoscopic surgery comprising a probe having an aspirating tip coupled by probe tubing to at least one collection canister, an overflow drain receptacle coupled by drain tubing to at least one collection canister, and a negative pressure source coupled to the at least one collection canister, a method for maintaining suction at the aspirating tip substantially constant at a level to withdraw the majority of the fluid flow from a surgical site into which the aspirating tip is inserted in endoscopic surgery, comprising the steps of:

aspirating fluid and organic debris from the surgical site through the probe and probe tubing into the at least one collection canister;

collecting overflow from a body orifice in communication via the overflow drain receptacle with the surgical site into the drain receptacle through the drain tubing and into the at least one collection canister;

holding the at least one collection canister under negative pressure and producing a suction force through the probe tubing and drain tubing by operation of the negative pressure source; and increasing the flow impedance of the drain tubing as compared to the flow impedance of the probe tubing to a level where the suction force in the probe tubing is larger than the suction force in the drain tubing, such that a majority of irrigation fluid at the surgical site is removed through the probe to minimize absorption of fluid within the patient and reduce overflow.

8. A method of assuring proper flows of irrigation fluid in performing a surgical procedure in a body cavity in which irrigation fluid flowing into the cavity is to be aspirated to a collection chamber to minimize absorption in the body while overflow under gravity to a drain receptacle from the cavity is also to be collected under suction in the collection chamber, comprising the steps of:

drawing the aspirated fluid toward the collection chamber via a first path having a first flow impedance, drawing the overflow toward the collection chamber from the drain receptacle via a second path having a second flow impedance higher than the first, combining the first and second paths to a common third path leading to the collection chamber, and establishing a suction level in the collection chamber sufficient to provide a desired suction level for aspiration in the body cavity.

9. A method of providing desired flow relationships between an aspiration path from the interior of a body cavity that is being irrigated with a fluid while overflow of fluid from the cavity drains initially under gravity into a collector, to reduce absorption of fluid within the body, comprising the steps of:

establishing a negative pressure collection volume;

providing a single negative pressure path from the collection volume;

splitting the single path into two subsequent paths, the first subsequent path being in communication with the collector and the second subsequent path being in communication with the aspiration path in the interior of the body cavity, and adjusting the flow of impedance of the first and second subsequent paths such that the impedance of the first path is selectively greater than the impedance of the second path.

* * * * *